United States Patent [19]

McDonald

[11] Patent Number: 5,920,317
[45] Date of Patent: Jul. 6, 1999

[54] SYSTEM AND METHOD FOR STORING AND DISPLAYING ULTRASOUND IMAGES

[75] Inventor: Omid McDonald, Ottawa, Canada

[73] Assignee: VMI Technologies Incorporated, Ottawa, Canada

[21] Appl. No.: 08/661,611

[22] Filed: Jun. 11, 1996

[51] Int. Cl.[6] .................................................. G06T 1/00
[52] U.S. Cl. ..................... 345/356; 345/348; 345/302; 707/512; 600/407; 705/3
[58] Field of Search ..................................... 345/302, 348, 345/356, 357; 128/653.1, 660.01; 395/200.3, 200.31; 707/512, 514, 104, 502; 600/437, 440, 407; 705/3

[56] References Cited

U.S. PATENT DOCUMENTS

| | | | |
|---|---|---|---|
| 5,307,456 | 4/1994 | Mackay ..................................... | 395/154 |
| 5,325,293 | 6/1994 | Dorne ................................. | 364/413.01 |
| 5,388,197 | 2/1995 | Rayner ..................................... | 395/154 |
| 5,452,416 | 9/1995 | Hilton et al. ............................. | 395/161 |
| 5,502,727 | 3/1996 | Catanzaro et al. ..................... | 370/94.2 |
| 5,522,067 | 5/1996 | Swire ...................................... | 395/600 |
| 5,583,980 | 12/1996 | Anderson ................................. | 395/173 |
| 5,600,775 | 2/1997 | King et al. ............................... | 395/806 |
| 5,617,539 | 4/1997 | Ludwig et al. ..................... | 395/200.02 |
| 5,619,995 | 4/1997 | Lobodzinski .......................... | 128/653.1 |
| 5,637,871 | 6/1997 | Piety et al. ............................... | 250/330 |
| 5,655,084 | 8/1997 | Pinsky et al. ............................. | 395/203 |
| 5,659,793 | 8/1997 | Escobar et al. .......................... | 395/807 |
| 5,664,087 | 9/1997 | Tani et al. ................................ | 345/473 |
| 5,785,043 | 7/1998 | Cyrus et al. .............................. | 128/712 |
| 5,786,814 | 7/1998 | Moran et al. ........................ | 345/326 X |

*Primary Examiner*—Joseph H. Feild
*Attorney, Agent, or Firm*—Hardaway Law Firm, PA

[57] ABSTRACT

A system for recording and displaying ultrasound images. The system includes a database server, an ultrasound image capture station and an ultrasound image review station. The ultrasound images are captured from an analog video signal stream output by an ultrasound machine and converted into compressed digital data preferably in MPEG format. The compressed digital data is archived to a compact disc recordable medium for permanent storage. The ultrasound images may be annotated by a sonographer as they are captured. The sonographer selects an annotation icon from a predefined list of icons to highlight points of interest in an ultrasound scan. The system also includes a demographic data module for tracking captured ultrasound scans, and a clinical data module for reporting ultrasound findings and diagnoses. The advantages include reduced storage requirements because of the elimination of video tape; more accurate tracking of ultrasound scans; easier review due to perfect still frames, random access, annotated highlights and zoom capability; faster more accurate reporting of findings and diagnosis; and, the ability to share ultrasound images over local and wide area networks.

22 Claims, 8 Drawing Sheets

Echocardiogram Report

Name: DEMO 2  
Chart: 7777123  
Referred by: Physician A  
Date of scan: 13/05/1996  
Indication(s):

Study Type: transthoracic;  
Sonographer: Physician B;  
Location: Lab;  
Procedure: complete study;

---

Measurements

| | | |
|---|---|---|
| Rv end-diastole (.7 - 2.3) | 1.0 cm LV systole (2.2 - 3.9) | 5.0 cm |
| IV Septum (.6 - 1.1) | 2.0 cm Aortic root diameter (2 - 3.7) | 6.0 cm |
| LV end-diastole (3.5 - 5.7) | 3.0 cm LA size (1.9 - 4) | 7.0 cm |
| LV post. wall (.6 - 1.1) | 4.0 cm | |

---

Findings

- mitral valve insufficiency/regurgitation
- normal right atrium
- normal left atrium
- normal left ventricle
- normal interventricular septum
- vegetation on the mitral valve

---

Diagnosis 1. normal left ventricle
2. mitral valve insufficiency/regurgitation
3. normal left atrium

Comments follow-up exam recommended in Nov. '96.

---

*Dr. D. Cosgrove M.D.*  
*June 3, 1996*

FIG. 8

SYSTEM AND METHOD FOR STORING AND DISPLAYING ULTRASOUND IMAGES

TECHNICAL FIELD

The present invention relates to the recordal and display of ultrasound images and, in particular, to a system and method for storing and displaying clinical ultrasound images so that the images may be readily retrieved, reviewed and/or annotated with pointers and/or clinical observations relevant to the images.

BACKGROUND OF THE INVENTION

Ultrasound is a non-intrusive diagnostic technique originally developed in the late 1950's. Using very high frequency sound waves, echo images are produced that are particularly useful for imaging many of the internal structures of living organisms. In recent years, the quality of ultrasound equipment has been improved and the equipment is now capable of producing images of outstanding detail and clarity. Unlike x-rays, ultrasound produces dynamic views which are especially useful in examining concealed structures which are subject to changes in shape or position, such as the human heart, human fetuses, the circulatory system and reproductive and internal organs. An ultrasound examination is generally referred to as a "scan", and will be so referred to in this document.

Traditionally, ultrasound scans have been stored on analog media as video images using a video cassette recorder to record the images on a video cassette tape. Those tapes are reviewed by physicians for diagnosis and are generally kept for reasons of clinical history and medical liability. It is well known that video tape has a long but limited shelf life. It is also known that the quality of video tape reproduction deteriorates over time. Furthermore, video tape is voluminous and requires substantial storage space. There are also other disadvantages associated with storing ultrasound images on video tape. For example, reviewing video tape must be done in a linear progression. In order to locate a particular sequence on the tape, the tape must be viewed sequentially, fast forwarded or rewound until the frames of interest are located. Besides, even with expensive video cassette recorders, still frames are generally of poor quality so that details shown in only a few frames may be difficult to detect and/or analyze for purposes of diagnosis. It is also difficult to annotate an ultrasound video recording since the only annotations that can be made during recording are voice recordings made by the sonographer or a physician present during the recording process. For many reasons, including the presence of the patient, the sonographer's ability to comment during an ultrasound scan is limited. Any observations made by the doctor after recording an ultrasound scan must be recorded on a separate medium and linked to the video tape as annotations using a video tape counter, which may be less accurate than desired if the video is later reviewed using a different video cassette recorder.

Hospitals are currently under pressure to operate more efficiently while improving the quality of care they provide. While ultrasound has become an increasingly important tool in assuring quality of care, the burden of capturing, recording and storing ultrasound images has not been much facilitated for many years. The current volume of usage of ultrasound as a diagnostic tool has made that burden onerous. Many vendors of ultrasound equipment now provide still frame and three second "cine loop" storage and display in order to facilitate diagnosis but there remain many problems associated with the capture and storage of ultrasound images. For example, technologists often waste time locating a patient's video tape and then spend more time winding the tape to a free recording space. After an ultrasound session is recorded, it must be reviewed by a physician for diagnosis, and reported. Reports are generally dictated by the physician and then typed by a transcriptionist. This requires time and skilled support staff, and introduces the possibility of stenographic and typographic errors.

There therefore exists a need for an improved, more versatile system of recording, storing and reviewing ultrasound images particularly ultrasound images used in clinical diagnoses in hospital environments.

SUMMARY OF THE INVENTION

It is an object of the invention to provide a system for digitally recording ultrasound images which can be accessed randomly or sequentially to eliminate time spent searching for a particular location in an ultrasound scan.

It is a further object of the invention to provide a system for storing and displaying ultrasound images that permits an ultrasound scan to be annotated during recordal so that points of interest can be tagged for later review.

It is yet a further object of the invention to provide a system for displaying ultrasound images in which a recorded ultrasound scan can be linked to related clinical finding or observation, and the link can be used to point to and retrieve a specific frame or series of frames related to the clinical finding.

It is a further object of the invention to provide a system for storing and displaying an ultrasound scan in which the images are recorded on compact disc recordable (CDR) to conserve storage space and substantially increase the shelf life of stored images.

It is yet a further object of the invention to provide a system for storing and displaying an ultrasound scan which permits physicians to create a diagnostic report of the scan using a simple point and click interface.

In its simplest form, the invention provides a method of storing and displaying ultrasound images comprising the steps of:
  a) capturing analog video signals of the ultrasound images and converting the analog signals into digital data representative of the ultrasound images;
  b) storing the digital data in a memory;
  c) retrieving the digital data from the memory on demand and converting the data into signals representative of the ultrasound images; and
  d) displaying the ultrasound images on a visual display surface.

In accordance with a further aspect of the invention there is provided an apparatus for displaying ultrasound images comprising, in combination:
  means for capturing analog video signals representing ultrasound images of a specific subject and converting the analog video signals into digital data signals representing the ultrasound images;
  means for associating the digital data signals with an identifier indicating the specific subject;
  means for storing the digital data signals and the identifier in a memory; and
  means for retrieving and reviewing on demand the digital data signals as full motion/still frame ultrasound images displayed on a display surface.

The present invention therefore provides a unique system for recording and storing ultrasound scans to facilitate the review, annotation and storage of the ultrasound images, as well as the production of clinical reports related to the ultrasound scan. The system preferably includes a database server and at least one personal computer configured with a demographic data module, a clinical data module, a ultrasound image capture module, a ultrasound image review module and a compact disc archival module. These modules function cooperatively to permit a user to capture, store, retrieve, review and annotate ultrasound scans. As a further enhancement, the system provides a unique report generating facility which comprises an intuitive data structure that permits physicians to record clinical findings using a point and click interface that generates reports automatically, eliminating any requirement for dictation and transcription.

BRIEF DESCRIPTION OF THE DRAWINGS

The invention will now be explained in more detail by way of example only, and with reference to the following drawings, wherein:

FIG. 8 is a sample clinical report automatically generated by the system in accordance with the invention.

DETAILED DESCRIPTION OF THE PREFERRED EMBODIMENT

Figure 1:
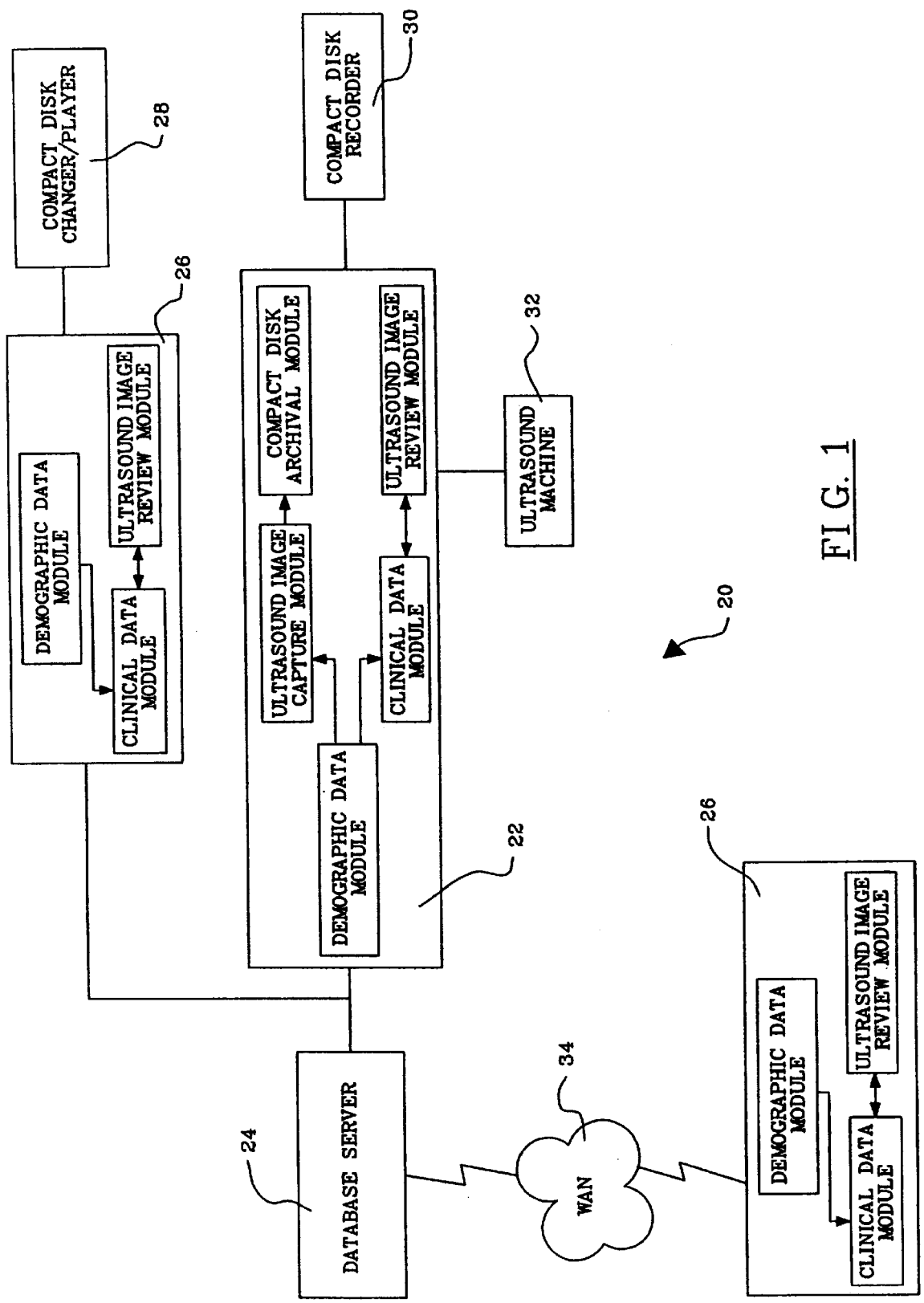
FIG. 1 is a block diagram of the system configuration for a system for storing and displaying ultrasound images in accordance with the invention.

FIG. 1 shows a block diagram of a preferred configuration for a system for storing and displaying ultrasound images in accordance with the invention, generally indicated by the reference 20. The system is organized in accordance with a client/server architecture, a network architecture well known in the art. The system includes the client components generally indicated by references 22, 26 and a database server component 24. Normally, the clients 22, 26 and the database server 24 are separate computing machines, although they may be one and the same. Preferably, both client machines 22, 26 are personal computers linked by a network operating system such as Microsoft NT, available from Microsoft Corporation, Seattle, Wash., U.S.A., or the like, to the database server 24 in a local area network (LAN). The system in accordance with the invention may also be configured to include a WAN 34 (Wide Area Network) and may include one or more clients 22, 26 remotely connected to the database server 24, or other system components. The WAN 34 may include the Internet, or any other pocket-switched service.

The construction and configuration of the computers 22, 24 and 26 and the networking software are well known in the art and do not constitute a part of this invention. The demographic data module, the ultrasound image capture module, the compact disc archival module, the ultrasound image review module, and the clinical data module installed in the client 22 constitutes the configuration for a workstation referred to below as a "capture station 22". The capture station 22 is capable of performing all functions in accordance with the invention. The system 20 may also include clients 26, referred to below as "review stations" 26. The review stations 26 may or may not be connected directly to a compact disc changer/player 28. Most network architectures support access to a remote compact disc changer/player so that a compact disc may be accessed through a remote workstation, in a manner well known in the art.

The capture station 22 includes all of the hardware and software tools required to capture, archive and review ultrasound images. Ultrasound machines output ultrasound images as an analog video signal stream. In order to provide all of the advantages of digital data storage and display, the capture station 22 converts the analog video signal stream into digital data which is stored in a digital data file. Because of the current restraints on the data handling capacity of personal computers, the digital data must be compressed during conversion. For this purpose, capture station 22 includes an encoder card (not illustrated) and an MCI (Multimedia Command Interface, furnished as a part of the Windows™ operating system available from Microsoft Corporation, Seattle, Wash., U.S.A.) for encoding, in real-time, analog ultrasound video output from an ultrasound machine 32. The encoder card preferably converts analog video signals into compressed digital data using conversion and compression algorithms known as MPEG. MPEG is a digital compression standard developed by the Motion Pictures Expert Group and has been adopted as ISO Standard 11172. An MPEG encoder card is available from, for example, FutureTel in Sunnyvale, Calif., U.S.A. The capture station 22 also includes a decoder card (not illustrated) used to display and control the MPEG video on a computer monitor display. The decoder card is also supplied with an MCI command set. Decoder cards are available, for example, from Sigma Designs of Freemont, Calif., U.S.A. The capture station 22 also includes software to enable the control of a compact disc recorder, such as a CDR 100™ available from the Yamaha Corporation of Japan. A software interface for controlling the compact disc recorder is available, for example, from Incatsystems of Campbell, Calif., U.S.A.

The system 20 therefore includes all the functionality necessary to identify a patient who is to be the subject of an ultrasound scan, create an admission record for the patient, capture the images output from the patient's ultrasound scan, archive the output to compact disc, review the captured scan images and generate a report which summarizes the measurements, findings and diagnosis resulting from the scan. The logical organization and function of each of these modules is described below.

Demographic Data Module

The demographic data module is a software application used to enter, edit and retrieve patient and patient admission information as it relates to ultrasound scans. The patient and patient admission database is stored on the database server 24 (see FIG. 1). As noted above, the database server adheres to client server methodology, which grants the server the only access to the central database. Capture stations 22 and review stations 26 make requests for information to the database server 24 which in turn retrieves the data. The principles of operation of this architecture are well known.

Figure 2:
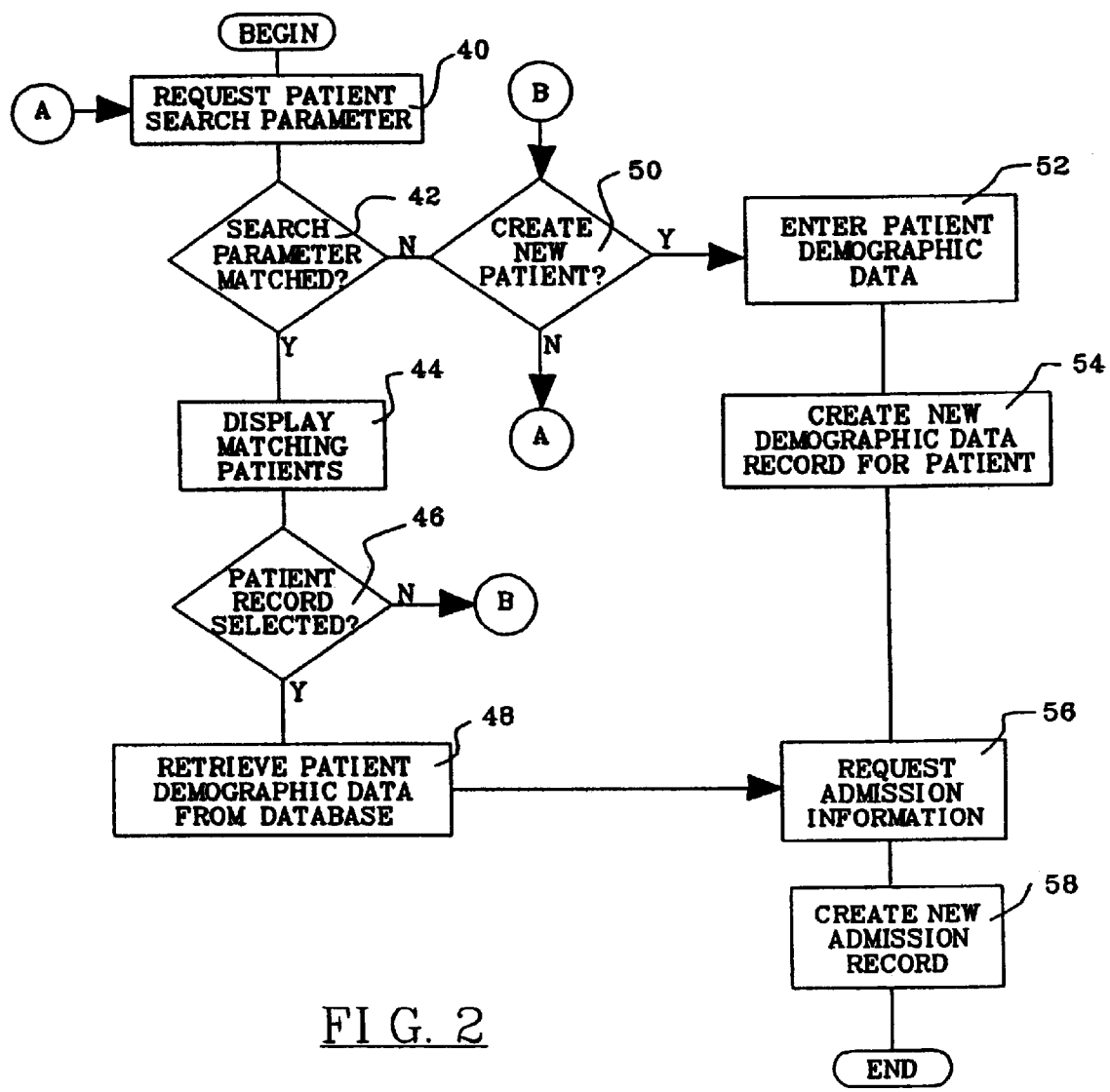
FIG. 2 is a flow diagram showing the principal operations performed by a demographic data module of the system shown in FIG. 1.

It is imperative that ultrasound scan facilities such as hospitals maintain impeccable records for identifying and tracking ultrasound scans to ensure that each scan is accurately and permanently associated with a specific patient and a specific date. In order to ensure that records are accurate and correctly associate each ultrasound scan with a specific patient, a demographic data module is provided with each capture station 22 and each review station 26. FIG. 2 shows a flow diagram of the principal functions of the demographic data module program. When the programs are executed, the demographic data module requests the user to enter a patient search parameter in a step 40. Preferably, the search parameter is a hospital chart number or the patient's surname, although other identifiers may be used as well. The search parameter is dispatched in a message to the database server 24 which searches for a match in the indicated field of the database. A return message is sent back to the demographic data module which determines in step 42 if the search parameter was matched. If the search parameter was matched, matching patients are displayed in step 44. The demographic data module then determines whether a patient record is selected from among the matching records as the correct record in step 46. If a patient record is selected, a message is sent from the demographic data module to the database server 24 to retrieve patient demographic data associated with the selected record from the database server 24 in step 48. If, in step 42, the search parameter is not matched, the demographic data module requests whether a new patient record is to be created and evaluates the response in step 50. If a new patient record is not to be created, the user is requested to enter a patient search parameter in step 40. If a new patient record is to be created, the user is presented with a data entry screen in step 52 and given the opportunity to enter the new patient's demographic data, which preferably includes the patient's hospital chart number, the patient's first and last names, the patient's date of birth, sex and any other demographic data deemed appropriate. After the user has completed all mandatory fields in the demographic data entry screen (not illustrated), the demographic data module creates a new demographic data record for the patient in step 54 by sending the new record to the database server 24 which updates the database. Associated with each patient record is one or more admission records. Each admission record preferably includes at least the name of the physician who requested the ultrasound scan, the name of the physician who is to evaluate the scan, the location where the scan was recorded (i.e. the ultrasound lab, the emergency room, etc.), and the date of the scan. That information is requested in step 56 after the patient demographic data is retrieved in step 48 or a new patient record is created in step 54. After all mandatory fields of the admission entry screen (not illustrated) are completed by the user in step 56, the demographic data module creates a new admission record in step 58.

Ultrasound Image Capture Module

The ultrasound image capture module is designed to control an MPEG encoder card in response to user commands regarding the recording an annotation of an analog video stream output from the ultrasound machine 32. Communication with the MPEG encoder card is accomplished through a graphic/user interface which uses an MCI command set provided with the card by the encoder card manufacturer. In accordance with the preferred embodiment of the invention, the MPEG data output by the encoder card is stored directly to magnetic hard disk on the capture station 22 (see FIG. 1), and later archived to a CDR disk after the ultrasound scan is completed.

Figure 3:
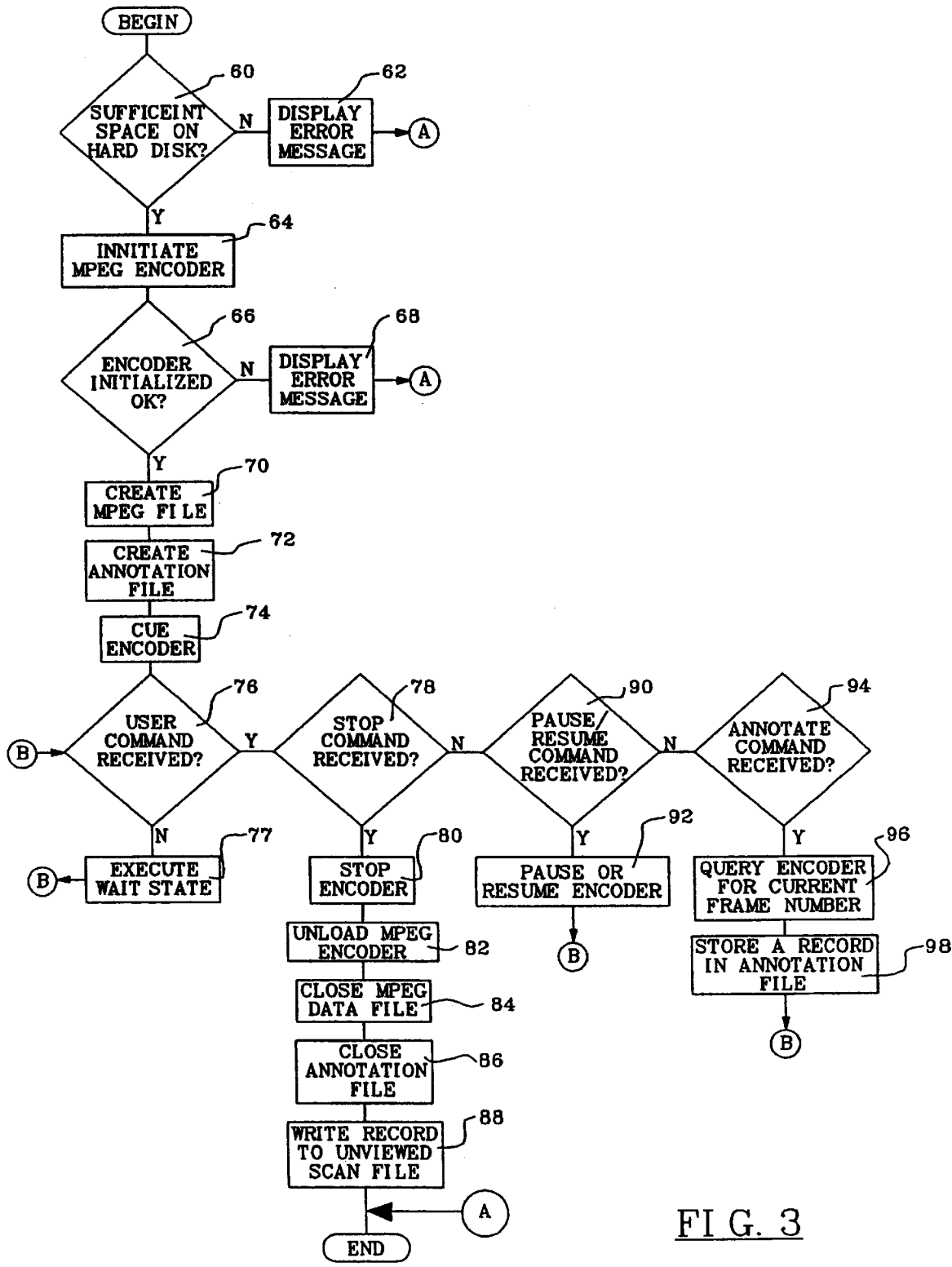
FIG. 3 is a flow diagram showing the principal operations of an ultrasound image capture module of the system shown in FIG. 1.

FIG. 3 is a flow diagram of the principal functions of the ultrasound image capture module. When a user begins an ultrasound scan capture session, the ultrasound image capture module checks the host hard disk of the capture station 22 to determine whether enough hard disk space is available to record forty minutes of ultrasound video in a step 60. Forty minutes is considered a maximum session length for an ultrasound study. Most studies are significantly shorter than that. If there is insufficient space on the capture station 22 hard disk, the ultrasound image capture module displays an error message in step 62 and the program ends. If sufficient hard disk space exists, the ultrasound image capture module initializes the MPEG encoder card in step 64 and determines in step 66 whether the encoder card initialized correctly. If the encoder card cannot be initialized in step 66, the ultrasound image capture module displays an error message in step 68 and the program ends. If the encoder card is successfully initialized, a file is created for the MPEG data on the host hard disk in step 70. Subsequently, an annotation file is created in step 72. The annotation file is used to store annotations created by a sonographer performing the ultrasound scan to indicate certain points of interest in the ultrasound images recorded. Table I shows the fields of the annotation file and a description of each field.

TABLE I

| FIELD | DESCRIPTION |
| --- | --- |
| Admission ID | A pointer (long integer) to the patient admission to which the scan is related. |
| Scan No. | The file name of the MPEG data file to which the annotation file is attached. |
| Annotation Type | A code indicating the annotation type. |
| Location | The MPEG video data frame number at which the annotation was made. |
| Scan Data | The calendar date on which the scan was made. |
| Sonographer ID | A pointer (long integer) to the sonographer (or other) who created the annotation. |

Preferably, the annotation file is assigned the same name as the MPEG data file but is assigned a different file extension, though another file naming convention can be used for locating and retrieving the annotation file. As may been seen in Table I, the file includes an annotation type which identifies an icon to be placed on a time line when the scanned images are reviewed. Annotations are used as pointers to direct physicians to points of interest or note in the recorded ultrasound image sequence. The function and use of annotations is described below. After the annotation file is created in step 72, the MPEG encoder is queued in step 74 and the ultrasound image capture module checks to see if a user command is received in step 76. If no command is received, the ultrasound image capture module executes a wait state in step 78 until a user command is received. In step 78, the ultrasound image capture module determines whether a user command received is a stop command. If so, the ultrasound image capture module stops the MPEG encoder in step 80, unloads the MPEG encoder in step 82, closes the MPEG data file in step 84, closes the annotation file in step 86, writes a record to an unviewed scan file in step 88 and ends the program. The unviewed scan file written to in step 88 is a record of all scans which have been recorded but not reviewed and is used in the ultrasound image review module to remind physicians of completed scans which have not been diagnosed, as will be explained below in more detail with reference to the description of the ultrasound image review module.

If it is determined in step 78 that the command received is not a stop command, the ultrasound image capture module determines in step 90 whether the command received is a pause or resume MPEG encoder command. If a pause or resume MPEG encoder command is received, the ultrasound image capture module responds by pausing or resuming the MPEG encoder in step 92 and returns to step 76 to await a subsequent user command. If in step 90 it is determined that a pause or resume MPEG encoder command was not received, the ultrasound image capture module determines in step 94 whether an annotate command was received. If an annotate command was not received, the ultrasound image capture module returns to step 76 to await a user command. If an annotate command is received in step 94, the ultrasound image capture module queries the MPEG encoder for the current frame number in step 96 and stores an annotation record in the annotation file created in step 72.

In the preferred embodiment of the invention, eight annotation types are accommodated. Each annotation type is indicated by a unique icon which is placed on a display time line when the ultrasound images are reviewed. The annotations are used by the sonographer to indicate points of interest or note in the ultrasound image recorded during the scan. Table II shows the eight annotation types, the icons associated with each annotation type and the indication which the annotation conveys to a skilled person reviewing the ultrasound images.

TABLE II

| ANNOTATION TYPE | ICON | INDICATION |
| --- | --- | --- |
| Start Cine | vertical bar | highlights start of a sequence of interest |
| End Cine | vertical bar | highlights end of a sequence of interest |
| Measure | ruler | measurement |
| Voice | microphone | voice recording |
| Flag | flag | indicates a frame of particular interest |
| Unknown | ? | indicates an unfamiliar motion or structure |
| View | eye | indicates a change of view |
| Summary | sheet of text | indicates location of scan summary |

The annotation types include "Start Cine" which is used to highlight a short motion sequence in the ultrasound image stream. Normally, a "cine loop", as it is known in the art, is used by the sonographer to highlight a cycle of interest or movement, for instance, the operation of a valve in a scanned human heart, or the like. In practice, if a sonographer observes a scanned image sequence of particular interest while moving an ultrasound transducer over a patient's body in a particular way, the sonographer will select the "start cine" button to create a start cine annotation record and repeat the movement of the transducer to capture the sequence for the physician who will review the recorded scan. When the sequence of interest has been recorded, the sonographer selects an "End Cine" annotation to highlight the end of a sequence of interest. A third annotation type is the "Measure" annotation which is indicated by a ruler icon when the sonographer takes a measurement during an ultrasound scan. Ultrasound machines are enabled to perform a plurality of measurements including a distance between two points, the slope of a doppler curve, the area of a two-dimensional plane defined by a boundary, or the like. Such measurements are made for diagnostic purposes. When a measurement is made, the sonographer may indicate the position of the measurement in the image sequence by selecting the Measure annotation. A fourth annotation type is the "Voice" annotation which is indicated by a microphone icon. This annotation type is selected by the sonographer when the sonographer records a voice comment while performing an ultrasound scan. Most ultrasound machines are enabled for voice recordal, though in practice the voice recordal function is seldom used in most institutions.

A fifth annotation type is the "Flag" which is represented by a flag icon and used to indicate one or more frames of particular interest. The flag annotation permits the sonographer to flag any frame(s) in the video which may show interesting or abnormal structure. A sixth annotation type is the "Unknown" annotation type represented by a question mark icon. The Unknown annotation type is used to indicate any motion or structure which is unfamiliar to the sonographer. A seventh annotation type is the "View" annotation type which is represented by an eye icon and is used to indicate a change of view. Normally, any ultrasound scan is performed in a specific sequence of so-called "views". In each view the transducer is moved over a specific part of the body. Diagnosis of the scan is facilitated if the physician has an indication of when the "view" is changed. The View icon provides a visual indication of that change. By noting the point in the scan at which the view changes, the physician can deduce by convention which view is being observed. The last type of annotation is the "Summary" annotation which is indicated by a sheet of text icon. The summary annotation is used to indicate the location of the scan summary in the recorded ultrasound images. Ultrasound machines store all measurements made during a scan and those measurements can be displayed together on a summary screen which is at or near the end of a scan. The Summary icon is used to pinpoint the location of the Summary screen so that a physician can readily locate it.

The use of annotation icons, which is more fully described below in the description of the ultrasound image review module, greatly facilitates the review of ultrasound scans by physicians. When combined with the capability for random access provided by digital image data, the improvement over prior analog storage and review methods is dramatic.

Compact Disc Archival Module

This module is designed to transfer the recorded digital video data from the hard disk of the capture station 22 to a Compact Disc Recordable (CDR). The annotation file is also copied to the CDR. The recorded compact disc therefore provides a complete record of the scan as will be further described below in relation to the ultrasound image review module.

Figure 4:
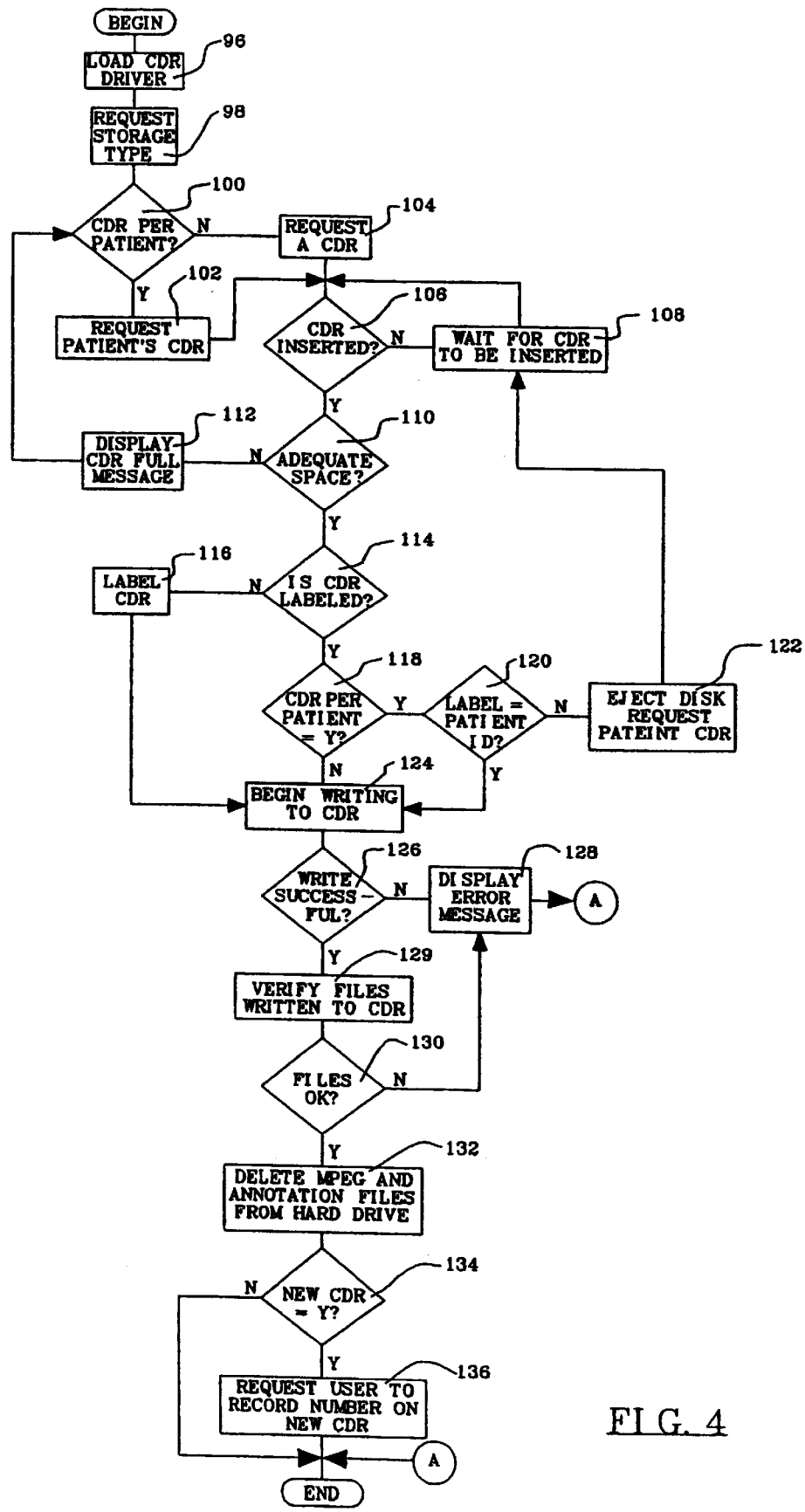
FIG. 4 is a flow diagram showing the principal operations of a compact disc archival module of the system shown in FIG. 1.

FIG. 4 shows a flow diagram of the principal functions of the compact disc archival module. The programs begin by loading a CD Recorder driver in a step 96. The compact disc archival module then requests the user to enter a storage type in step 98. In accordance with the preferred embodiment of the invention, a scan may be saved on a compact disc for each patient, or on any available compact disc. It is preferred that scans be stored on a compact disc per patient basis since this facilitates tracking and does not significantly increase cost. In step 100, the compact disc archival module determines whether the storage type is to be on a compact disc per patient basis. If so, the patient's CDR is requested in step 102 and if not, a CDR is requested in step 104. In either case, the compact disc archival module determines in step 106 whether a CDR has been inserted and if not, waits in step 108 for the CDR to be inserted. After the CDR is inserted, the compact disc archival module examines the available space on the CDR in step 110 to determine whether it is adequate space to store the MPEG video file and the annotation file. If the space is not adequate, the compact disc archival module displays a CDR full message in step 112 and returns to step 100. Otherwise, this compact disc archival module determines in step 114 whether the CDR is labelled. If there is no label on the CDR, the CDR is labelled in step 116 and the compact disc archival module begins writing to the CDR in step 124. If the CDR is labelled, the compact disc archival module checks the CDR per patient flag in step 118. If that flag is set to yes, the compact disc archival module determines whether the label matches the patient ID in step 120. If the label does not match the patient ID, the CDR is ejected in step 122 and the system returns to step 108 to wait for a CDR to be inserted. If the CDR label matches the patient ID in step 118, compact disc archival module begins writing to the CDR in step 124. In step 126, the compact disc archival module determines whether the write is successful. If the write is unsuccessful, an error message is displayed in step 128 and the program ends. If the write is successful, the MPEG video data file and the annotation file written to the CDR are verified in step 129. If the files do not verify correctly in step 130, an error message is displayed in step 128 and the program ends. If the files do verify correctly, both the MPEG data file and the annotation file are deleted from the capture station 22 hard disk in step 132 and a new CDR flag is checked in step 134 to determine whether the CDR was new or had been used before, as indicated by the label writing process in step 116. If the CDR is new, the CDR is ejected and a message is displayed in step 136 to request the user to record an identification number on the CDR. The program then ends and all allocated resources are released.

Ultrasound Image Review Module

The ultrasound image review module handles the retrieval and display of captured MPEG and annotation files. An MPEG decoding card and MCI command set is used to decode and display the MPEG data on a computer display monitor (or a television monitor, or the like). The MCI commands permit the application to respond to requests from a user to pause, resume, seek to any frame in the video sequence and to set the frame display rate of the ultrasound images. Since digital video, such as MPEG video enables random access to video, a simple way of permitting a user to select a particular point in the ultrasound scan is required. This requirement is fulfilled by constructing a time line which is displayed as a horizontal bar where each horizontal pixel represents one second of video play time at 30 frames per second, the default display rate. For example, an ultrasound scan of 4 minutes and 20 seconds would be represented by a time line measuring 260 pixels in length. When a user clicks on the time line using a mouse, the ultrasound image review module determines the pixel at which the mouse click occurred and seeks a corresponding point in the MPEG data file. For example, if the user clicks on the 64th pixel, the MPEG data is retrieved from the 64th display second in the data file.

Figure 5:
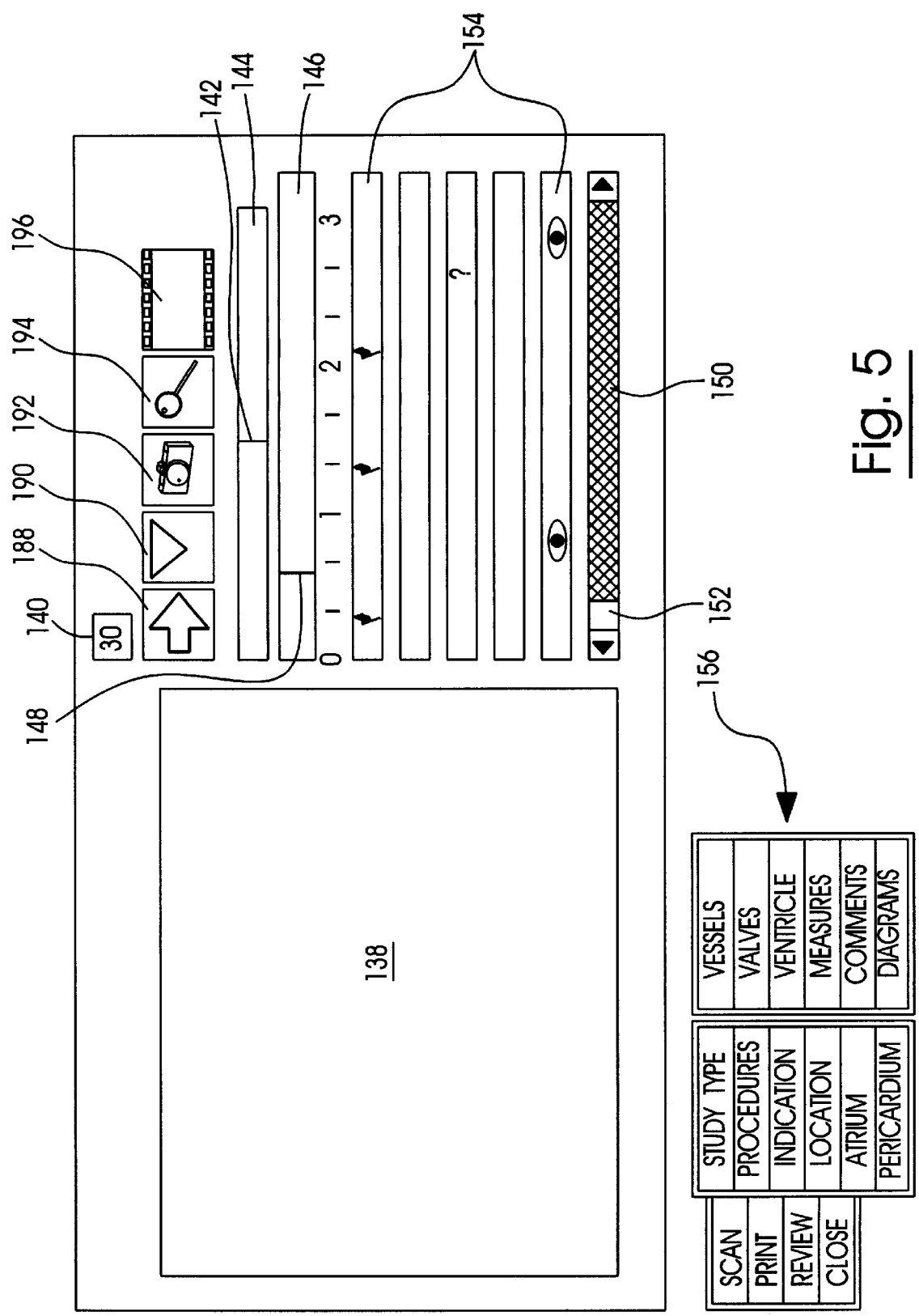
FIG. 5 is a preferred configuration for an ultrasound image review screen in accordance with the invention.

FIG. 5 shows a preferred configuration for an ultrasound image review screen in accordance with the invention. The screen includes a display area 138 where ultrasound images are displayed. The ultrasound images are displayed at a user definable display rate. The default display rate is the international movie standard of 30 frames per second. The display rate is displayed adjacent a top right hand corner of the ultrasound image display area 138 in a frame rate display area 140. The frame display rate may be adjusted by dragging a vertical display rate indicator 142 along a horizontal display rate bar 144 in order to change the display rate from a minimum of one frame per second to a maximum of 64 frames per second. Spaced below the display rate bar 144 is a display time line 146 which is preferably about 180 pixels in length so that it displays the current three minutes of the ultrasound scan being displayed. A vertical display time indicator 148 shows the position of the current display in the displayed sequence. A scroll bar 150 shows the current position relative to the total length of the ultrasound scan. As in any Windows™ application, the scroll button 152 can be dragged to any point in the sequence to move the display to that point. Likewise, the display time indicator 148 can be dragged to a new point on the display time line 146 to move the display to that point in the ultrasound images, or the user may click on the time line to move the display to the point indicated by the mouse pointer. As the ultrasound images are displayed beyond the three minute mark, the numerals 0, 1, 2 and 3 displayed below the display time line 146 scroll to the left and are replaced by the numerals 4, 5, 6, etc. Spaced below the display time line 146 are preferably five annotation time lines 154. As will be explained below in more detail, when an ultrasound scan is loaded for display, the annotation time lines are populated with annotations entered by the sonographer when the ultrasound scan was performed. A plurality of annotation time lines are used in order to provide adequate space for the annotations and to eliminate confusion if several annotations are closely grouped together. The uppermost annotation time line 154 is preferably used for flags (see Table II), the second is preferably used for start and end cine symbols, the third is preferably used for unknown type annotations and voice annotations, the fourth is preferably used for measure annotations and the fifth is used for new view and summary annotations. A person reviewing an ultrasound scan may move to any annotated frame in the scan by clicking on the appropriate annotation icon with the mouse, as will also be explained below.

Positioned under the display area 138 are a plurality of clinical data buttons generally indicated by the reference 156. The clinical data buttons are related to the clinical data module which is explained below in detail. Located above the frame rate control bar 144 is a toolbar which includes five buttons. The functions of the five toolbar buttons will be explained below in more detail.

Figure 6:
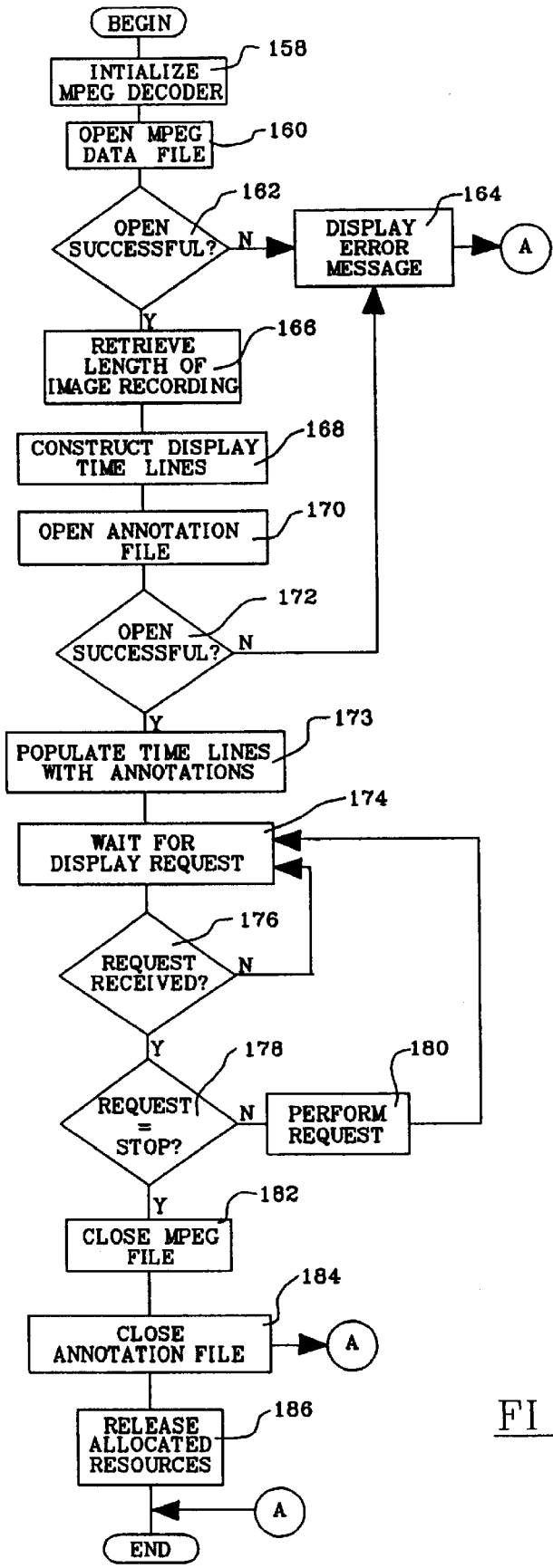
FIG. 6 is a flow diagram showing the principal operations of an ultrasound image review module shown in FIG. 1.

FIG. 6 is a flow diagram of the principal operations of the ultrasound image review module. When the program is begun, the software application initializes the MPEG decoder card in a step 158. The application then opens the MPEG data file in step 160. If the file opening is determined not to have been successful in step 162, an error message is displayed in step 164 and the program is terminated. If the file opening is determined to be successful in step 162, the MPEG card is used to retrieve the length of the ultrasound image recording in step 166 and the application constructs the display time line 146 (see FIG. 5) in step 168. The application then opens the annotation file in step 170. If the annotation file opening is determined not to be successful in step 172, an error message is displayed in step 164 and the program is ended. If in step 172 the file opening is determined to be successful, the application constructs the annotation time lines 154 (see FIG. 5) and populates the annotation time lines in step 173 with the annotations indicated by the annotation records in the annotation file opened in step 170. The application then waits for a user display request in step 174 if a request is received in step 176, the application determines whether the request equals stop displaying ultrasound images in step 178. If the request is not equal to stop, the selected user option is performed in step 180 and the program is returned to step 174. If the request is a stop display request, the MPEG data file is closed in step 182, the annotation file is closed in step 184, allocated resources are released in step 186 and the display program ends.

Table III shows a list of user options which can be selected as display requests in step 174 and performed in step 180. Column 1 shows the user request, column 2 shows the source of the request, column 3 shows the system response.

TABLE III

| User Request | Source of Request | System Response |
|---|---|---|
| Start | Click on start button | Begin an ultrasound scan review session |
| Pause/Resume | Click on pause/resume icon on toolbar | Pause/resume playback |
| Maximize display window | Click on maximize icon on tool bar | Maximizes display area |
| Set frame rate | Click on frame rate control bar | Increase/decrease frame display rate per request |
| Seek to position | Click on time line; click on time line scroll bar; click on an annotation shown on the annotation time lines | Compute new position from time line or annotation file and send start display command to decoder |
| Copy current frame to still window | Click on camera icon on toolbar | Create new still image object from current video frame |
| Replay still frames in sequence | Click on film icon on toolbar | Replay still image objects in order created |
| Zoom/unzoom window | Click on zoom icon on toolbar | Command decoder to zoom/unzoom display area |

Referring once again to FIG. 5 at the top of the display control portion of the display screen is a tool bar which contains five icons which are also used to control the display sequence. The user can request action from any of the icons as shown in Table III. The pause/resume icon 188 is indicated by a right arrow which permits a user to pause or resume play of ultrasound images at any point in a review. A maximize display icon 190 is used to maximize the size of the image display area 138 for a larger view of ultrasound images. A capture still icon 192, which looks like a camera, is used to capture a still view of the current frame being displayed in the display area 138. The captured still is stored as a copy of the current contents of the display area of the screen image memory. Any number of still images may be captured during an ultrasound image review session. The captured still images are saved for the duration of the session but are not saved after the session is ended. A zoom/unzoom icon 194, which looks like a magnifying glass, is used to zoom in and zoom out the current image displayed in the image display area 138. A replay stills icon 196, which has the appearance of a strip of film, is used to replay all of the still images captured to that time in the order of their capture. This tool bar enables physicians to manipulate ultrasound images to their advantage in diagnosing an ultrasound scan. In addition, as noted above, a physician may seek to any position in the ultrasound scan system by clicking on the display time line 146 or on any annotation icon displayed on any of the annotation time lines 154. This permits a physician reviewing the ultrasound session to move quickly in any direction to a specific frame or sequence of frames in the ultrasound scan. This eliminates the time consuming and frustrating task of fast forwards and rewinds of analog video tape and greatly facilitates review and diagnosis.

Clinical Data Module

In order to further facilitate the analysis and the reporting of ultrasound studies, a clinical data module was designed to permit physicians to enter a wide variety of clinical findings using a capture station 22 or a review station 26 (see FIG. 1). A "point and click" reporting system based on a tree-like structure is used to provide a simple way for a physician to navigate to the diagnosis they need.

Figure 7:
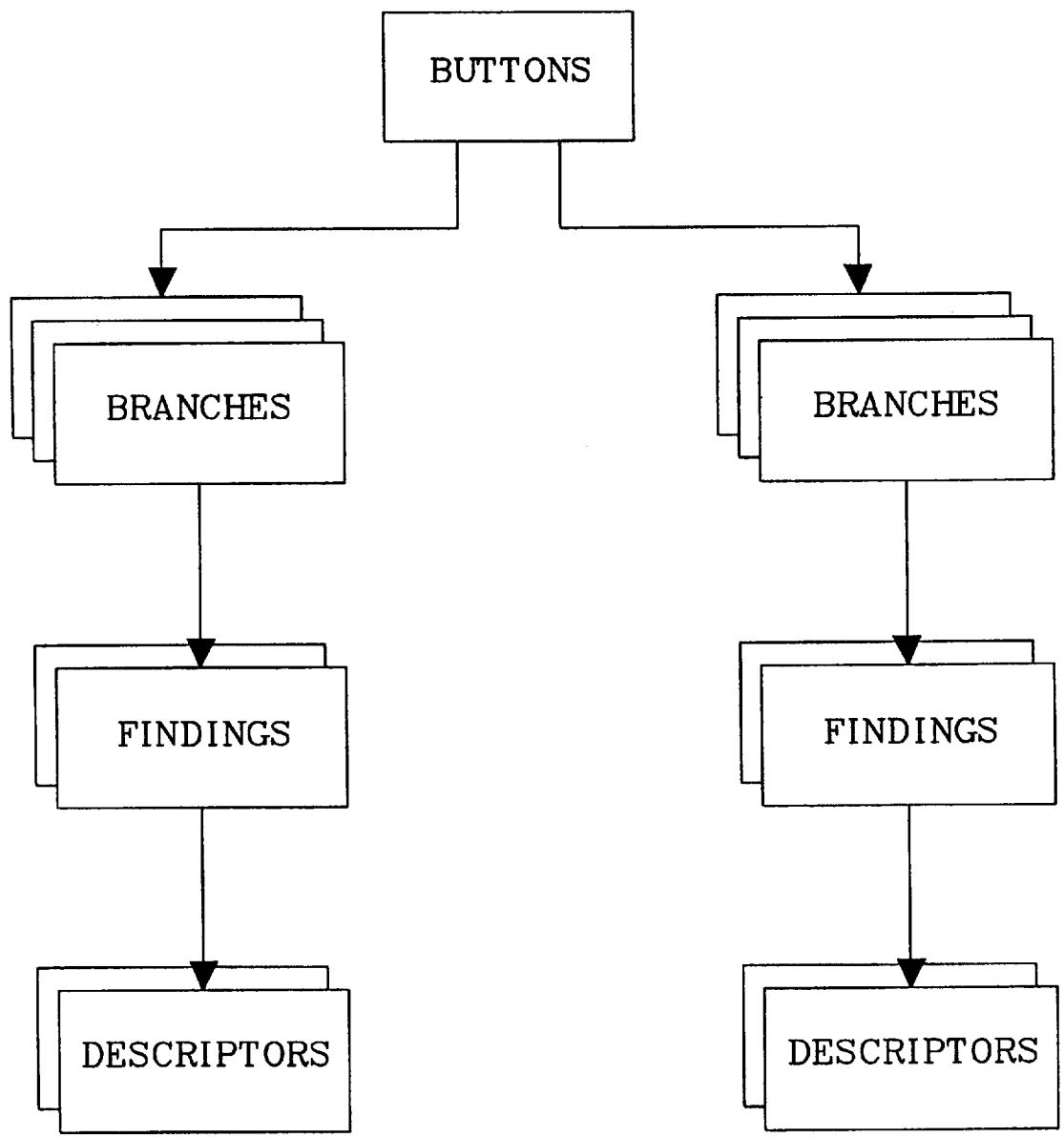
FIG. 7 is a schematic diagram of a tree structure for specifying clinical findings and generating clinical reports related to ultrasound scans.

FIG. 7 is a diagram of the tree structure developed for this application. Situated at the top of the tree are buttons which are related to branches. The branches are related to findings, which may be related to descriptors. The tree contents are user definable and adapted to support any clinical discipline that requires ultrasound scans. The clinical data buttons 156 (see FIG. 5) are normally defined as anatomical structures, such as atrium, pericardium, vessels, valves and ventricles, for example. While the buttons shown in FIG. 5 relate to cardiology, as noted above, the tree contents are user specifiable and any clinical discipline may be incorporated into the tree structure including obstetrics, pediatrics, etc. Each button is followed by any number of branches until the required finding is located. A final branch in the tree provides a descriptor which may be used to automatically generate a report of the findings and diagnosis of an ultrasound scan. Shown below is a sample tree transversal for the atrium of a human heart:

Button Branch Findings Descriptor

| Button | Branch | Findings | Descriptor |
|---|---|---|---|
| Atrium | Right | Calcified | Mild |
|  | Left | Clot | Moderate |
|  |  | Enlarged | Severe |
|  |  | Regurgitation |  |

This sequence generates the finding, moderate left atrial enlargement. This tree-like structure is created by the interaction of two database tables, a Sequence table and an Elements table. The Sequence table provides a means of traversing the tree while the Elements table stores the description of a finding. The Sequence table includes the following fields: NodeID, GroupID, DataID and NextGroup. The Elements table includes the following fields: DataID, Label and Text. The two tables are transparent to a user, such as a physician using the tree structure to report a scan diagnosis. The physician uses a computer mouse to point to and select a button relating to the anatomical structure which is a subject of his report. When the physician selects a finding by clicking on the following branches, findings and descriptors, the finding is stored in a database table called the EntryData table. Only a pointer to the selected finding is saved, not the text of the finding. By saving a pointer to the finding, the amount of storage space required in the database is minimized. The EntryData table includes the following fields: EntryID, AdmissionID, DataID, Ultrasound Image Frame and Value. The frame field allows findings to be associated to a particular frame in an ultrasound video. The value field allows the finding to be associated with a measurement, such as a doppler slope, a heart wall thickness, or the like, for example.

The purpose of the clinical data module is to permit physicians to enter a wide variety of clinical findings in a simple and intuitive manner. This is accomplished by dividing the diagnostic process into the tree-like structure described above. For example, the major chamber in the human heart is the atrium. The atrium is divided into left and right chambers called the left atrium and the right atrium. Within the left atrium, a physician may make several findings, one of which may be an enlarged left atrium. This finding, the enlarged left atrium may be further qualified by recording the amount of enlargement, such as a "severely enlarged left atrium". Each of the major anatomical structures associated with each ultrasound discipline are displayed as buttons. By clicking on a button, a list of qualifiers or subcategories is displayed. For example, clicking on the atrium button will display a list containing left and right. These branches permit more precise specification of a button. As noted above, the atrium is divided into left and right chambers. Each chamber has certain attributes which may be stored in further subcategories etc. Shown below are several typical entries from a Sequence table created for the human heart:

| GroupID | DataID | NextGroup | What is displayed |
|---|---|---|---|
| 205 | 1200 | 310 | Atrium |
| 310 | 1877 | 387 | right |
| 310 | 1878 | 388 | left |
| 388 | 1950 | 0 | normal |
| 388 | 1952 | 410 | enlarged |
| 388 | 1953 | 0 | calcific |
| 388 | 1951 | 0 | thickened |
| 410 | 2220 | 0 | mild |
| 410 | 2221 | 0 | moderate |
| 410 | 2222 | 0 | severe |

The DataID field in the Sequence table links the Sequence and the Element tables. The NextGroup field is used to determine the elements to be displayed in the next branch of the tree. For example, if a physician points to and clicks on the "atrium" button (see FIG. 5), the branches "right" and "left" in NextGroup 310 (see Sequence table above) are displayed to the right of the buttons 156 shown in FIG. 5. If the physician then clicks on "left" the NextGroup 388 element of "normal", "enlarged" "calcific" and "thickened" are displayed to the right of the "right" and "left" branches. If "enlarged" is selected from group 388, the NextGroup 410 is displayed to the right of group 388. The elements of group 410 include "mild", "moderate" and "severe". Group 410 has no NextGroup, so no further group is displayed when "moderate" is selected from that group, and the DataID 2221 for the finding "moderately enlarged left atrium" is stored in the EntryData table. If all the branches of a tree will not fit simultaneously on the screen shown in FIG. 5, the display scrolls to the left as new branches are selected until there are no more branches to display and the finding is saved to the EntryData table.

The purpose for separating the tree transversal information found in the Sequence table from the textual information found in the Elements table is for language translation. The entire database can be translated by changing the text in the Elements table without rebuilding the traversal information. Some typical records in the Elements table are displayed below:

| DataID | Label | Text |
|---|---|---|
| 1200 | Atrium | Atrium |
| 1877 | right | right atrium |
| 1878 | left | left atrium |
| 1950 | calcified | calcified left atrium |
| 1951 | clot | clot in the left atrium |
| 1952 | enlarged | enlarged left atrium |
| 1953 | regurgitation | left atrial regurgitation |
| 2220 | mild | mild left atrial enlargement |
| 2221 | moderate | moderate left atrial enlargement |
| 2222 | severe | severe left atrial enlargement |

When a finding is chosen, the DataID field is stored in a data table associated with the patient's file. For example, when a physician selects "moderate left atrial enlargement" the following record in the data table is added:

| AdmissionID | DataID | Frame | Value |
|---|---|---|---|
| 8829 | 221 | | |

The AdmissionID field contains a link to the patient admission for which the finding was entered. The frame field is used to link a finding to a particular ultrasound image frame (if applicable). The value field is used to store information to findings that require numerical data (such as measurements). Saving the patient information in the demographic data module permits a diagnosing physician to review the findings of previous scans for purposes of comparison to assess deterioration/regeneration. This simple tree structure permits physicians to quickly select a diagnosis using point and click techniques without any requirement to dictate diagnosis to tape or use transcriptionists. If the physician wishes to create freeform text aside from the options provided by the clinical data module tree structure, the physician can select the comments buttons from the clinical data buttons 156 (see FIG. 5) which permits the physician to enter freeform text through the keyboard of the review station 26. The physician can also select the "diagrams" which displays a diagram of the human heart, for example, to permit the physician to select appropriate descriptors from an associated list provided with each section of the organ.

While the preferred embodiment of the invention has been described in relation to cardiology ultrasound, it should be understood that the invention can be equally well applied to any other discipline which requires ultrasound scans and is in no way limited to studies involving cardiology or any other discipline.

Changes and modifications to the preferred embodiment described may be apparent to those skilled in the art. The invention is therefore intended to limited only by the scope of the appended claims.

I claim:

1. Apparatus for displaying ultrasound video images comprising, in combination:

means for capturing analog video signals representing ultrasound images of a specific subject and converting the analog video signals into digital data signals representing the ultrasound images;

means for associating the digital data signals with an identifier indicating the specific subject;

means for storing the digital data signals and the identifier in a memory;

means for retrieving and reviewing the digital data signals as full motion/still frame video images displayed on a display surface;

means for associating an annotation with one or more frames of the video images, the annotation being stored in an annotation file associated with the data, and including fields to identify an annotation type and an image frame number to identify the image frame in the digital data to which the annotation is related;

the annotation type identifying an icon associated with the annotation type; and the annotation icon being displayed on an annotation time line when the digital data is queued for review.

2. Apparatus for displaying ultrasound video images as claimed in claim 1 wherein an image frame identified by the image frame number is displayed on the display surface when an associated annotation icon is selected using a pointing device connected to the apparatus.

3. A system for storing and displaying clinical ultrasound images as claimed in claim 1 wherein means for retrieving and reviewing the digital data signals is an ultrasound image review module which includes a decoder card for decoding the compressed digital data output by the encoder card so that the ultrasound images can be displayed on a display surface.

4. A system for storing and displaying clinical ultrasound images as claimed in claim 3 wherein the ultrasound image review module includes a decoder card for decoding the compressed digital data in MPEG format output by the encoder card so that the ultrasound images can be displayed on a display surface.

5. Apparatus for displaying ultrasound video images comprising, in combination:

means for capturing analog video signals representing ultrasound images of a specific subject and converting the analog video signals into digital data signals representing the ultrasound images;

means for associating the digital data signals with an identifier indicating the specific subject;

means for storing the digital data signals and the identifier in a memory;

means for retrieving and reviewing the digital data signals as full motion/still frame video images displayed on a display surface; and means for generating a report of clinical findings and diagnosis related to a particular ultrasound scan to which the ultrasound images are related, including a point and click interface for selecting findings relevant to the particular ultrasound scan to which the ultrasound images are related, the point and click interface including a data tree in which buttons indicate anatomical structures and branches for specifying and describing the anatomical structures.

6. Apparatus for displaying ultrasound video images as claimed in claim 5 wherein the data in the data tree is user specifiable.

7. Apparatus for displaying ultrasound video images as claimed in claim 5 wherein the data tree is defined by two files, a tree traversal information file and a data definition file linked to the tree traversal information file by a linking field.

8. Apparatus for displaying ultrasound video images as claimed in claim 7 wherein all descriptive text is stored exclusively in the data definition file so that a translation of the descriptive text into another language changes all descriptive displays of the information when the translated information is loaded into the data definition file.

9. Apparatus for displaying ultrasound video images as claimed in claim 5 wherein a record is stored in a data file associated with the ultrasound scan when the data tree is traversed and a finding is selected.

10. Apparatus for displaying ultrasound video images as claimed in claim 9 wherein the records in the data file are used in conjunction with patient demographic data to generate on demand a report of a diagnosis of an ultrasound scan.

11. A system for storing and displaying clinical ultrasound images associated with an ultrasound scan, comprising, in combination:

at least one database server for storing patient data related to the ultrasound images;

at least one ultrasound capture station for capturing an analog video image stream from an ultrasound machine and converting the analog video image stream into digital data representative of the ultrasound video images, the capture station including means for displaying the ultrasound images;

means for networking the database server and the capture station so that the database server and the capture station can communicate; and a clinical data module having a point and click interface to facilitate reporting a diagnosis of the ultrasound scan, the point and click interface including a data tree structure for storing clinical data relevant to the ultrasound scan, and descriptive phrases may be selected for inclusion in a report by traversing the data tree by selecting successive elements from the tree using a computer pointing device connected to the capture station.

12. A system for storing and displaying clinical ultrasound images as claimed in claim 11 wherein the data tree includes two data files, a first file for storing tree traversal data and a second file for storing descriptive data related to the tree traversal data.

13. A system for storing and displaying clinical ultrasound images as claimed in claim 12 wherein each tree traversal record includes a field that stores an index of a next group to be displayed for selection when a member of a current group of the traversal data is selected.

14. Apparatus for displaying ultrasound video images, comprising:

an ultrasound image review screen having an ultrasound image display area and a plurality of annotation time lines displayed outside the ultrasound image display area, the plurality of annotation time lines providing a display area for annotation icons which are displayed in a relative position on the plurality of annotation time lines to indicate a relative position of an annotation associated with the annotation icon in the video images; and each of the respective annotation time lines is used to display one or more predefined types of annotation icon, each respective type of annotation icon being associated with only one annotation time line.

15. Apparatus for displaying ultrasound video images, as claimed in claim 14 further comprising:

a frame rate display area for displaying a number representative of a current number of frames per second at which the ultrasound video images are being displayed; and a frame rate display bar and a frame rate display indicator which may be dragged along the frame rate display bar to change, within a predefined range, the frame rate at which the ultrasound images are displayed.

16. Apparatus for displaying ultrasound video images as claimed in claim 15 further including an image display time line, which represents at least a significant portion of a total length of the ultrasound video images for a captured ultrasound scan as a graphical bar and a pointer on the bar to show a point on the bar representative of a current position in the images equivalent to an elapsed time given a sequential review of the images.

17. Apparatus for displaying ultrasound video images as claimed in claim 15 further including a user tool bar with selectable user buttons for:

a) pause/resume of the ultrasound video image display;

b) maximize/minimize ultrasound image display area;

c) create a still image object from currently displayed video frame;

d) replay still frames in sequence; and e) zoom/unzoom display image.

18. Apparatus for displaying ultrasound video images, comprising:

an ultrasound image review screen having an ultrasound image display area; and a point and click interface to facilitate reporting a diagnosis of the ultrasound scan, the point and click interface including a data tree structure for storing clinical data relevant to the diagnosis of the ultrasound scan, and descriptive phrases selectable for inclusion in a diagnostic report by traversing the data tree while selecting successive elements from the tree using a point and click device.

19. Apparatus for displaying ultrasound video images as claimed in claim 18 wherein the data tree structure includes two data files, a first file for storing tree traversal data and a second file for storing descriptive data related to the tree traversal data.

20. Apparatus for displaying ultrasound video images as claimed in claim 19 wherein each record in the tree traversal data includes a field for storing an index of a next group to be displayed for selection when a member of a current group of the traversal data is selected.

21. Apparatus for displaying ultrasound video images as claimed in claim 18 wherein the clinical data is stored in a database table that stores an ultrasound image frame value.

22. Apparatus for displaying ultrasound video images as claimed in claim 21 wherein when a clinical finding is retrieved from the database of clinical data, clicking on the clinical finding causes an ultrasound image associated with the ultrasound image frame value to be displayed on the ultrasound image display area.

* * * * *